United States Patent
Oettel et al.

(10) Patent No.: US 6,432,939 B1
(45) Date of Patent: Aug. 13, 2002

(54) 17A-HYDROXY-4-ANDROSTENE-3-ONE AND DERIVATIVES THEREOF

(76) Inventors: Michael Oettel, Beethovenstrasse 30, 07743 Jena; Jens Berlau, Gotthardtstrasse 17, 99084 Erfurt; Wolfgang Römer, Iltisweg 39; Gerhard Schreiber, An der Trebe 14, both of 07749 Jena, all of (DE)

( * ) Notice: Subject to any disclaimer, the term of this patent is extended or adjusted under 35 U.S.C. 154(b) by 0 days.

(21) Appl. No.: 09/710,427

(22) Filed: Nov. 10, 2000

Related U.S. Application Data

(60) Provisional application No. 60/168,324, filed on Dec. 2, 1999.

(51) Int. Cl.⁷ .............................. A61K 31/56; C07J 53/00
(52) U.S. Cl. ........................................ 514/178; 550/510
(58) Field of Search ................................ 514/178, 179; 552/510, 638

(56) References Cited

U.S. PATENT DOCUMENTS 3,917,829 A * 11/1975 Voigt et al. .................. 424/242

* cited by examiner

*Primary Examiner*—Barbara P. Badio
(74) *Attorney, Agent, or Firm*—Wood, Phillips, Katz, Clark & Mortimer

(57) ABSTRACT

This invention describes 17α-hydroxy-4-androstene-3-one and its derivatives of the general formula I

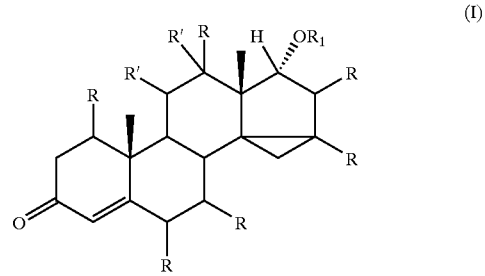

a method for producing these compounds and pharmaceuticals containing these compounds. The compounds according to the invention can be used for regulating spermatogenesis and for hormone replacement therapy in males by stimulating the inhibin-B secretion by the Sertoli cells. The increased inhibin-B concentration suppresses spermatogenesis in the testicles as it inhibits excretion by the hypophysis of follicle-stimulating hormone (FSH) that is essential in spermatogenesis.

11 Claims, 2 Drawing Sheets

Inhibin-B secretion by Sertoli cells (1 x 10$^6$) after adding FSH (300 ng/1) as a function of time. The average values displayed here represent 4 series of measurements.

Inhibin-B secretion by Sertoli cells (1 x 10⁶) after adding 17α-hydroxy-4-androstene-3-one (epitestosterone; EpiT; 1μM) as a function of time. The average values displayed here represent 2 series of measurements.

17A-HYDROXY-4-ANDROSTENE-3-ONE AND DERIVATIVES THEREOF

This application claims the priority of Provisional Appln. No. 60/168,324, filed Dec. 2, 1999.

This invention relates to 17α-hydroxy-4-androstene-3-one and its derivatives, methods for their production, and pharmaceuticals containing these compounds.

It is known from the state of the art that natural testosterone and follicle-stimulating hormone (FSH) are important regulatory components of spermatogenesis. As the gametes themselves have no FSH receptors, hormonal signals have to be transferred via Sertoli cells that produce unknown signals required for spermatogenesis (de Kretser D. M. et al., Hum. Reprod., 1998, 13, pp. 1–8). The FSH concentration is regulated using inhibin-B (negative feedback) that is released from the Sertoli cells. Inhibin-B itself inhibits the secretion of FSH, thereby suppressing spermatogenesis. This is why inhibin-B is considered to be a marker of spermatogenesis (Pierik F. H. et al., J. Clin. Endocrinol. Metab., 1998, 83, pp. 3110–3114) and why it plays a vital role in the paracrine and endocrine regulation of spermatogenesis as a function of its concentration. A correlation of inhibin-B and sperm concentration has also been reported (Klingmuller D. et al., Hum. Reprod., 1997, 12, pp. 3276–3278; Jensen D. K. et al., J. Clin. Endocrinol. Metab., 1997, 82, pp. 4059–4063).

Epitestosterone, an androgene that is secreted in the testicles, has long been regarded as an inactive epimer of testosterone. It has been found in the past few years, however, that it has either an inhibiting or an increasing effect on FSH levels in the plasma depending on its dose (Bicikova M. et al., J. Steroid. Biochem. Mol. Biol., 1993, 45, pp. 321–324). In this context, epitestosterone is described as a competitive inhibitor of androgen receptors (antiandrogen) (Lapcik O. et al., J. Endocrinol., 1994, 143, pp. 353–358; Starka L. et al., Vnitr. Lek., 1996, 42, pp. 620–623). In addition, it has been described that epitestosterone inhibits epididymal and prostatic 5α-reductase (Monsalve A. and Blaquier J. A., Steroids, 1977, 30, p. 41–51; Starka L. et al., J. Steroid. Biochem., 1989, 33, pp. 1019–1021). Starka et al. discussed an assumed connection between antiandrogenic activity and 5α-reductase inhibition (Starka L. et al., J. Steroid. Biochem., 1989, 33, pp. 1019–1021). Furthermore, it influences the conversion of testosterone into estrogens by aromatization (Broulik P. D. et al., Bone, 1997, 20, pp. 473–475).

It is one of the problems of this invention to provide known and new compounds with high efficacy for contraceptive uses and for hormone replacement therapy in men.

This problem is solved according to the invention by providing 17α-hydroxy-4-androstene-3-one or its derivatives of the general formula I

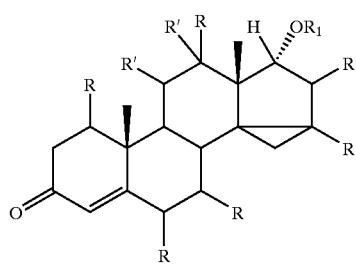

(I)

wherein
the residues R each independently represent a hydrogen atom or an $OR_2$ residue, where
the $R_2$ residues independently represent hydrogen atoms, saturated or unsaturated, straight-chain or branched alkyl or acyl groups containing 1 to 6 C atoms,
$R_1$ is a saturated or unsaturated, straight-chain or branched acyl group containing 1 to 18 C atoms, a benzoyl, methylbenzoyl, or alkylbenzoyl group containing up to 10 C atoms, a sulfite or a glucuronyl residue, and each R' residue represents a hydrogen atom or form a double bond together with the single bond between $C_{11}$ and $C_{12}$, and their pharmaceutically tolerable salts.

It is preferred according to the invention that $R_1$ is an undecanoyl, lauroyl, tridecanoyl, myristoyl, pentadecanoyl, palmitoyl, acetyl, caproyl, benzoyl, valeroyl, sulfite, or glucuronyl residue.

The compounds according to the invention of the general formula I can be administered either in their free form or as pharmacologically effective salts. Suitable examples of these salts of compounds of the general formula I include addition salts of common physiologically compatible inorganic and organic acids such as hydrochloric acid, hydrobromic acid, phosphoric acid, sulfuric acid, oxalic acid, maleic acid, fumaric acid, lactic acid, tartaric acid, malic acid, citric acid, salicylic acid, adipinic acid, and benzoic acid. Other acids that can be used are described, for example, in Arzneimittelforschung, vol. 10, pp. 224–225, Birkhäuser Verlag, Basel and Stuttgart, 1966, and in Journal of Pharmaceutical Sciences, vol. 66, pp. 1–5 (1977).

The addition salts of acids are obtained in a generally known way by intermixing the free base or its solutions with the respective acid or its solutions in an organic solvent such as methanol, ethanol, n-propanol, or isopropanol, or a lower ketone such as acetone, methyl ethyl ketone, or methyl isobutyl ketone, or an ether such as diethyl ether, tetrahydrofurane, or dioxane. Mixtures of the solvents mentioned above can be used to improve crystallization. In addition, physiologically compatible aqueous solutions of acid addition salts of the compound of the general formula I can be produced in an aqueous acidic solution.

The acid addition salts of compounds of the general formula I can be converted into the free base in a generally known way, e. g. using alkalies or ion exchangers. Other salts can be obtained by reacting the free base with inorganic or organic acids, especially such acids that are suited for forming therapeutically applicable salts. These and other salts of the new compound such as picrate can also be used to purify the free base by converting it into a salt, isolating this salt, and releasing the base from it.

The new derivatives of the invention of 17α-hydroxy-4-androstene-3-one are produced by partial synthesis (see Tetrahedron Lett. 35, p. 2329 (1994)). To do this, 14,15-unsaturated 17α-hydroxy-4-androstene-3-one is reacted with methyl dihalides and a zinc-copper pair or diazomethane and zinc iodide to the respective 14α, 15α-methylene-17α-ols. The derivatives of the invention that contain a 14,15-methylene group are synthesized with knowledge of the chemical reactions described in German patent no. DE 42 39 946. Alternatively, you the following method can be applied: To maintain an existing 17-oxo grouping, transform the derivative into ethylene ketal. The following steps are adding bromine to produce the respective 16α bromine compound and transformation into the $\Delta^{15}$ compound in a hydrobromination step. After isomerization to produce the $\Delta^{14}$ compound and splitting up said compound, the existing 17-oxosteroids are reduced with complex metal hydrides or diborane in a tetrahydrofurane solution at −10 to +10° C. Various substituents can be inserted, for example, at positions 11 or 12, again by partial synthesis. A suitable oxygen function is inserted in the molecule by adding ceric ammonium nitrate (see Terahedron Lett. 35, p. 8599 (1994)).

Another object of this invention are pharmaceutical preparations for oral, parenteral, topical, rectal, subcutaneous, intravenous, intramuscular, intraperitoneal, intranasal, intrabuccal or sublingual application which, in addition to the common substrates and diluents, contain as active ingredient at least one compound according to the invention of the general formula I or its acid addition salt.

The pharmaceuticals of the invention are produced in a generally known way using the common solid or liquid substrates or diluents and the commonly used adjuvants of pharmaceutical engineering, their dosage depending on the intended application. Preferred preparations are forms of application suitable for oral administration. Such forms of application include tablets, film tablets, lozenges, capsules, pills, powder, solutions or suspensions, or depot systems.

Parenteral preparations such as injection solutions can also be taken into consideration, of course. Another example of suitable preparations are suppositories.

The respective tablets can be produced, for example, by intermixing the active ingredient with known adjuvants, e. g. inert diluents such as dextrose, sugar, sorbitol, mannite, polyvinylpyrrolidone, blasting agents such as corn starch or alginic acid, binding agents such as starch or gelatin, lubricants such as magnesium stearate or talc and/or agents for producing a depot effect such as carboxyl polymethylene, carboxylmethyl cellulose, cellulose acetate phthalate, or polyvinyl acetate. The tablets may also consist of multiple layers.

Accordingly, lozenges can be produced by coating the cores produced in a similar way as the tablets with agents that are typically used in lozenge coatings, e. g. polyvinylpyrrolidone or shellac, gum arabic, talc, titanium dioxide, or sugar. The lozenge coating may consist of multiple layers, and the adjuvants listed above for tablets can be used here as well.

Solutions or suspensions with the active agent of the invention may further contain sweetening agents such as saccharin, cyclamate or sugar as well as aromatizers such as vanillin or orange extract. They may further contain suspending agents such as sodiumcarboxymethyl cellulose or preservatives such as p-hydroxybenzoates. Capsules containing active ingredients can be produced, for example, by mixing the active agent with an inert carrier such as lactose or sorbitol and encapsulating it in gelatin capsules.

Suitable suppositories can be produced, for example, by intermixing with the respective substrates such as neutral fats or polyethylene glycol or their derivatives.

Moreover, transdermal systems are an object of this invention. Such systems are sticking plaster, patches or topical forms of application as well as injectable implants. The manufacturing of such systems is known to the expert skilled in the art.

The advantages of this invention result from the fact that new pharmaceutical preparations for regulating spermatogenesis and for hormone replacement therapy are provided which contain active ingredients that have a novel profile of efficacy and/or a high efficacy as regards stimulation of inhibin-B.

BRIEF DESCRIPTION OF THE DRAWING

The advantageous effect of the compounds according to the invention as stimulators of inhibin-B secretion is shown in FIG. 2.

The compounds of the invention were compared to FSH at optimized test levels (FIG. 1).

Figure 1:
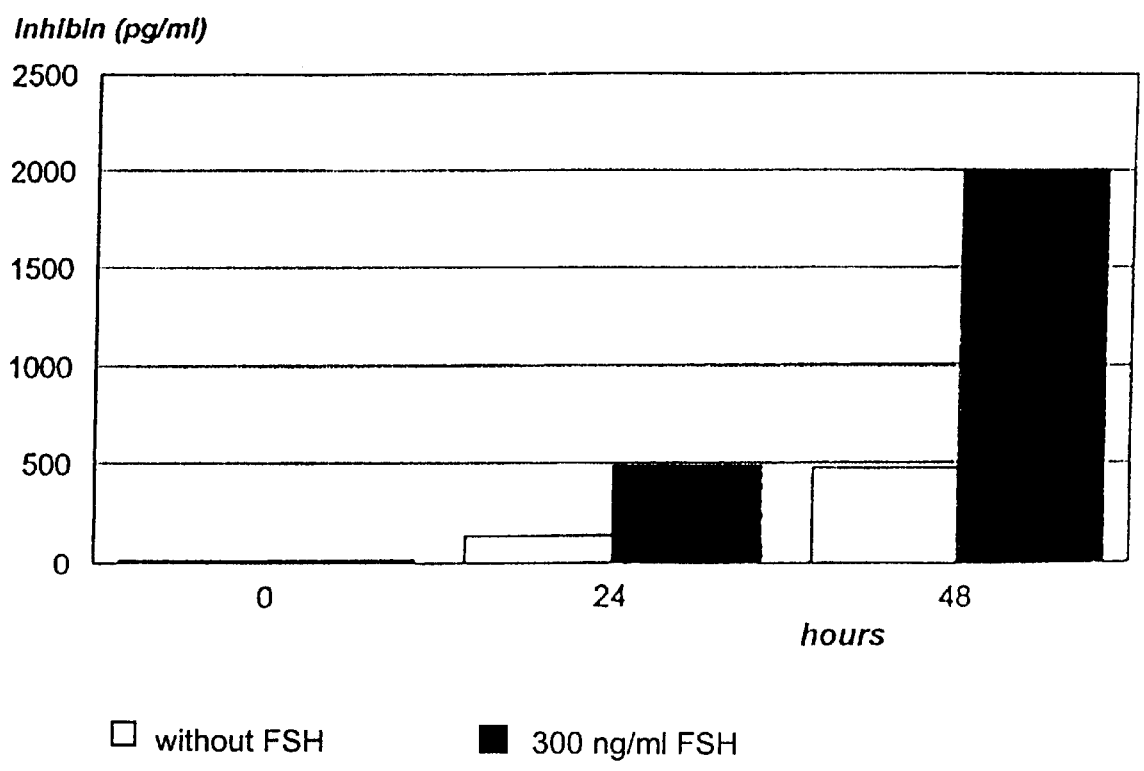
FIG. 1 shows the inhibin-B secretion by Sertoli cells ($1 \times 10^6$) after adding FSH (300 ng/l) as a function of time. The average values displayed here are the mean of the test results of 4 independent experiments.
Figure 2:
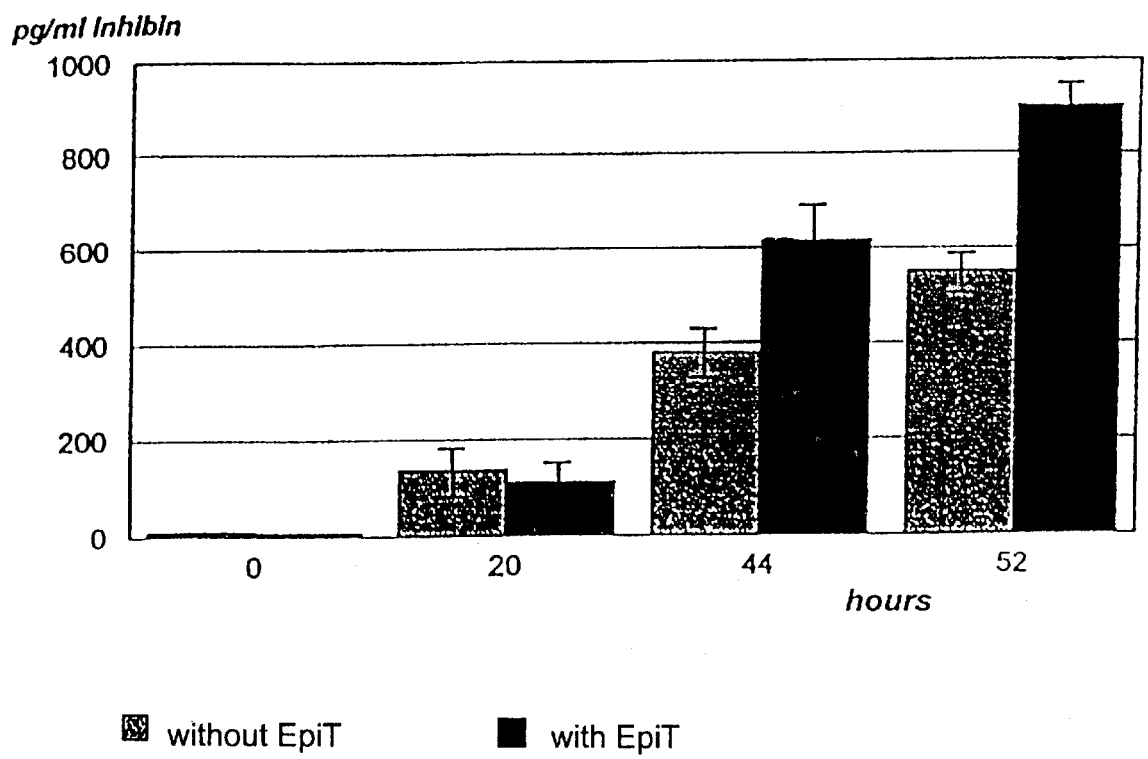
FIG. 2 shows inhibin-B secretion by Sertoli cells ($1 \times 10^6$ per ml of medium) after adding the substance of the invention, 17α-hydroxy-4-androstene-3-one (epitestosterone; EpiT; 1 uM), mean values from 2 series of measurement.

The in-vitro stimulating effect on inhibin-B generation was measured using inhibin-B dimer assays by Serotec, Oxford, UK. The statement on increased inhibin-B values characterizes the efficacy of the respective compound (FIG. 2). The difference between the released inhibin-B quantity with and without the test substance expresses the efficacy of the respective test substance.

The goal was to find out to what extent compounds according to the invention of the general formula I consisting of 17α-hydroxy-4-androstene-3-one and its chemically modified derivatives as well as its esters and salts, preferably sulfate and glucuronide conjugates can be used to stimulate the secretion of inhibin-B and thus indirectly suppress FSH levels to regulate spermatogenesis. As FSH is an important component of spermatogenesis, it is assumed that its inhibition reduces or suppresses the required endocrine stimulation of spermatogenesis.

Series of tests in Sertoli cell cultures that were free from hormones and steroids have shown that these cells release an increasing basal inhibin-B quantity for between 20 and 92 hours.

It was found, surprisingly, that after adding 17α-hydroxy-4-androstene-3-one or its derivatives of the general formula I according to the invention, inhibin-B levels expressed from the culture supernatant were significantly increased as compared to the control tests (FIG. 2) within an incubation time of 44 and 52 hours. This effect was particularly striking at epitestosterone concentrations in the range from 10 nM to 1 pM. However, when the steroids from natural sources such as progesterone, testosterone and dihydrotestosterone were added, inhibin-B secretion was not influenced.

The following example shall explain the invention in greater detail:

EXAMPLE

Study of the Pharmacological Efficacy of Sertoli Cell Stimulators on Inhibin-B Secretion The substances were tested for their stimulating effect on inhibin-B secretion in an in-vitro model using Sertoli cells originating from Wistar rats and cultivated for up to 4 days.

Collection of the Biological Material

Wistar rats that were 18 days old were killed using $CO_2$; their testicles were collected and mechanically chopped up using a surgical knife. The resulting cell pulp was enzymatically disintegrated with collagenase II, hyaluronidase, and DNase using the following method: The cell pulp was digested for 15 minutes at 37° C. in 20 ml of Dulbecco's Modified Essential Medium (DMEM) containing 20 mg of collagenase II; subsequently, it was sedimented for 7 minutes at room temperature. The supernatant was discarded. The remaining pellet was resuspended in DMEM, then sedimented again for 7 minutes. The next steps were a second decomposition for 30 minutes at 37° C. in 20 ml of DMEM containing 40 mg of collagenase II, 40 mg of hyaluronidase, and 0.1 mg of DNase, and a centrifugation step at 500 rpm. After washing in DMEM without additives and another centrifugation step, the pellet was a third time enzymatically disintegrated for 30 minutes at 37° C. in 20 ml of DMEM containing 40 mg of collagenase II, 40 mg of hyaluronidase and 0.1 mg of DNase, then centrifuged at 1,000 rpm. The pellet was then resuspended, washed once in DMEM without additives, and finally sublimated with 100 U/ml of penicillin, 100 µg/ml of streptomycin, 5 µg/ml of human transferrin, 2 µg/ml of insulin, 50 ng/ml of vitamin A (all from Sigma Co.), 200 ng/ml of vitamin E (Merck Co.), and 3 mg/ml of cytosine arabinoside (Sigma Co.) (DMEM-Z) and sowed in 24-well microtiter plates. After 48 hours, the cultivated cells were given hypotonic treatment using 20 mM of Tris-HCl (pH 7.4) to remove residual gametes, then the medium was changed into DMEM-Z.

Cell Culture Preparation 1 ml of biological sample containing $10^6$ Sertoli cells in 990 ml of DMEM-Z and test substances at a concentration range from 0.1 nM to 1 µM, each dissolved in 10 µl of absolute ethanol (1% w/v of the total batch) was incubated for 48 hours at 34° C. and 5% $CO_2$. The culture supernatant was then decanted from the cells, frozen at −20° C. and kept until the inhibin-B level was determined.

Reaction Batch 0.1 ml of culture supernatant was mixed with 0.05 ml of SDS of the inhibin-B assay (Serotec, Oxford, UK) in 1.8 ml Eppendorf reaction vessels and heated for 3 minutes to 100° C. After the batch had cooled down, 0.1 ml of assay diluent and 0.05 ml of a 6% $H_2O_2$ solution were added, intermixed, then incubated for 30 minutes at room temperature.

80 ml of the above reaction mixture and 80 ml of the 7 inhibin-B standards for creating a calibration curve contained in the assay were pipetted into the wells of the microtiter plate contained in the assay and allowed to incubate at room temperature overnight. Finally the wells were washed 3 times with an inhibin washing buffer.

The content of the alkaline phosphatase-conjugated antibody against human inhibin-B contained in the assay was taken up in 6 ml of assay diluent, and 0.05 ml of this solution were pipetted into the wells and incubated for 3 hours at room temperature.

Subsequently, the reaction charges are washed 8 times in washing buffer as described above, incubated in this buffer for 15 minutes, and washed another 3 times. Then 0.05 ml of the substrate solution contained in the assay are added to each well and incubated for 1 hour at room temperature. After this, 0.05 ml of the amplifier solution contained in the assay are added. When the batch shows a red coloration, the absorption values at 620 nm are measured against predosage level. When the inhibin-B standard of 1,000 pg/ml carried along while creating the calibration curve has reached an absorption of 2.0, the reaction is terminated using the stopper solution that comes with the assay, and the values for each reaction preparation are recorded. The cell culture batch that does not contain any test substance but contains ethanol as a vehicle is used as reference value.

We claim:

1. Derivatives of 17α-hydroxy-4-androstene-3-one of the general formula I

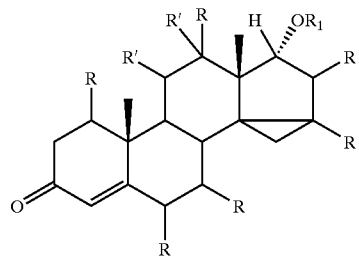

(I)

wherein
the residues R each independently represent a hydrogen atom or an $OR_2$ residue, where
the $R_2$ residues independently represent hydrogen atoms, saturated or unsaturated, straight-chain or branched alkyl or acyl groups containing 1 to 6 C atoms,
$R_1$ is a saturated or unsaturated, straight-chain or branched acyl group containing 1 to 18 C atoms, a benzoyl, methylbenzoyl, or alkylbenzoyl group containing up to 10 C atoms, a sulfite or a glucuronyl group,
and the R' residues each represent a hydrogen atom or form a double bond together with the single bond between $C_{11}$ and $C_{12}$,
or their pharmaceutically tolerable salts.

2. The derivatives according to claim 1 wherein $R_1$ is an undecanoyl, lauroyl, tridecanoyl, myristoyl, pentadecanoyl, palmitoyl, acetyl, caproyl, benzoyl,; valeroyl, sulfite, or glucuronyl residue.

3. A method for producing derivatives of 17α-hydroxy-4-androstene-3-one of the general formula I

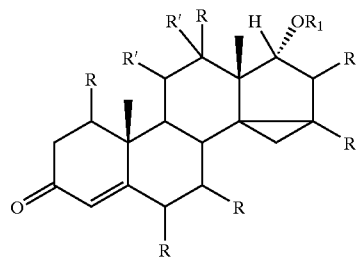

(I)

wherein the R, $R_1$, $R_2$, and R' residues are as defined in claim 1, and wherein 14,15-unsaturated 17α-hydroxy-4-androstene-3-one is reacted with methyldihalides and a zinc-copper pair of diazomethane and zinc iodide to produce the respective derivative 14α, 15α-methylene-17α-ols.

4. A method for producing derivatives of 17α-hydroxy-4-androstene-3-one according to claim 3, wherein 14,15-unsaturated-17α-hydroxy-4-androstene-3-one is obtained by transformation of 17-oxo-4-androstene-3-one into ethylene ketal, wherein a respective 16α-bromine compound is produced in a bromine addition step followed by a hydrobromination step to produce a $\Delta^{15}$ compound, and wherein the 17-oxosteroids obtained after isomerization of this compound to a $\Delta^{14}$ compound and subsequent splitting up are reduced using complex metal hydrides or diborane in a tetrahydrofurane solution at a temperature between −10 to +10° C.

5. The method according to claim 3 wherein an oxygen function is inserted by reacting with ceric ammonium nitrate (IV).

6. The method according to claims 4 wherein an oxygen function is inserted by reacting with ceric ammonium nitrate (IV).

7. Pharmaceutical preparations characterized in that they contain as an active ingredient at least one compound or its pharmacologically effective salt according to claim 1.

8. A pharmaceutical preparation for regulating spermatogenesis and for hormone replacement therapy in males comprising derivatives of 17α-hydroxy-4-androstene-3-one of the general formula I

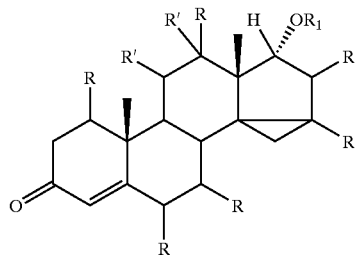

(I)

wherein
the residues R each independently represent a hydrogen atom or an $OR_2$ residue, where
the $R_2$ residues independently represent hydrogen atoms, saturated or unsaturated, straight-chain or branched alkyl or acyl groups containing 1 to 6 C atoms,
$R_1$ is a saturated or unsaturated, straight-chain or branched acyl group containing 1 to 18 C atoms, a benzoyl, methylbenzoyl, or alkylbenzoyl group containing up to 10 C atoms, a sulfite or a glucuronyl group,
and the R' residues each represent a hydrogen atom or form a double bond together with the single bond between $C_{11}$ and $C_{12}$,
or their pharmaceutically tolerable salts.

9. A pharmaceutical preparation for regulating spermatogenesis and for hormone replacement therapy in males comprising derivatives of 17α-hydroxy-4-androstene-3-one of the general formula I

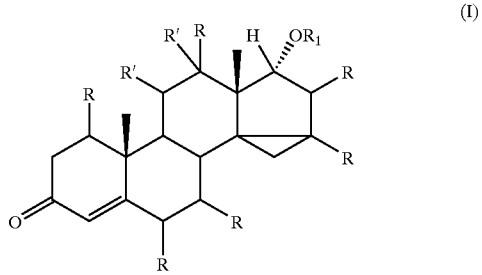

(I)

wherein
the residues R each independently represent a hydrogen atom or an $OR_2$ residue, where
the $R_2$ residues independently represent hydrogen atoms, saturated or unsaturated, straight-chain or branched alkyl or acyl groups containing 1 to 6 C atoms,
$R_1$ is an undecanoyl, lauroyl, tridecanoyl, myristoyl, pentadecanoyl, palmitoyl, acetyl, caproyl, benzoyl, valeroyl, sulfite, or glucuronyl residue,
and the R' residues each represent a hydrogen atom or form a double bond together with the single bond between $C_{11}$ and $C_{12}$,
or their pharmaceutically tolerable salts.

10. The pharmaceutical preparation according to claim 8, wherein said preparation is applied by means of an oral, parenteral, topical, rectal, subcutaneous, intravenous, intramuscular intraperitoneal, intranasal, intrabuccal or sublingual application.

11. The pharmaceutical preparation according to claim 9, wherein said preparation is applied by means of an oral, parenteral, topical, rectal, subcutaneous, intravenous, intramuscular intraperitoneal, intranasal, intrabuccal or sublingual application.

* * * * *